US007014632B2

(12) United States Patent
Takino et al.

(10) Patent No.: US 7,014,632 B2
(45) Date of Patent: Mar. 21, 2006

(54) PANTS-TYPE DISPOSABLE WEARING ARTICLE

(75) Inventors: Shunsuke Takino, Kagawa-ken (JP); Toshifumi Otsubo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 487 days.

(21) Appl. No.: 10/146,226

(22) Filed: May 15, 2002

(65) Prior Publication Data

US 2002/0173764 A1 Nov. 21, 2002

(30) Foreign Application Priority Data

May 18, 2001 (JP) ............................. 2001-148898

(51) Int. Cl.
*A61F 13/15* (2006.01)
(52) U.S. Cl. ..................................... 604/393; 604/402
(58) Field of Classification Search ..............................
604/385.24–385.31, 396–402, 393, 385.04
See application file for complete search history.

(56) References Cited

U.S. PATENT DOCUMENTS

| | | | | |
|---|---|---|---|---|
| 3,452,753 A | * | 7/1969 | Sanford | 604/401 |
| 3,771,524 A | * | 11/1973 | Ralph | 604/398 |
| 4,246,900 A | * | 1/1981 | Schroder | 604/368 |
| 4,657,539 A | * | 4/1987 | Hasse | 604/385.25 |
| 4,795,452 A | * | 1/1989 | Blaney et al. | 604/385.27 |
| 4,846,825 A | | 7/1989 | Enloe et al. | |
| 5,445,627 A | * | 8/1995 | Mizutani et al. | 604/385.28 |
| 5,607,416 A | * | 3/1997 | Yamamoto et al. | 604/397 |
| 5,906,603 A | * | 5/1999 | Roe et al. | 604/385.24 |
| 6,120,486 A | * | 9/2000 | Toyoda et al. | 604/385.29 |
| 6,120,488 A | * | 9/2000 | VanRijswijck et al. | 604/385.28 |
| 6,616,644 B1 | * | 9/2003 | Mizutani | 604/385.04 |
| 6,648,868 B1 | * | 11/2003 | Sayama et al. | 604/385.22 |
| 6,706,029 B1 | * | 3/2004 | Suzuki et al. | 604/385.28 |
| 2002/0143313 A1 | * | 10/2002 | Tsuji et al. | 604/385.03 |
| 2003/0078556 A1 | * | 4/2003 | Sasaki et al. | 604/385.25 |
| 2003/0144644 A1 | * | 7/2003 | Murai et al. | 604/385.27 |
| 2004/0002690 A1 | * | 1/2004 | Miyamoto | 604/385.25 |

FOREIGN PATENT DOCUMENTS

| | | |
|---|---|---|
| EP | 0 648 482 A | 4/1995 |
| EP | 0 945 111 A | 9/1999 |
| JP | 7-155344 | 6/1995 |
| WO | WO 00 53140 A | 9/2000 |

* cited by examiner

*Primary Examiner*—Michele M. Kidwell
(74) *Attorney, Agent, or Firm*—Butzel Long

(57) ABSTRACT

A pants-type disposable wearing article has a holder means and an absorbent pad means. The absorbent pad means has a crotch region extending to a front and rear waist regions of the holder means and has longitudinal front and rear ends attached to the front and the rear waist regions. The absorbent pad means has a liquid absorbent core and is provided with leak-barrier flaps rising from side edges of the core and a ribbon-like suspenders attached to the top edges of the leak-barrier flaps. The extensions of the suspenders from the front and rear ends of the absorbent pad means are connecting the top edges of the leak-barrier flaps with the inner surface of the front and rear waist regions of the holder means.

8 Claims, 8 Drawing Sheets ed with the holder means to define the pair of leg-holes and front and rear ends attached to the front and rear waist region respectively. The pants-type disposable wearing article further comprises a pair of leak-barrier flaps included in the absorbent pad means and locating immediately outside of the opposite side edges of the liquid-absorbent core, extending in the longitudinal direction of the absorbent pad means and adapted to rise from the opposite side edges and a pair of suspender means lying on top edges of the leak-barrier flaps, extending outwardly of the leak-barrier flaps in the longitudinal direction of the absorbent pad means and connecting the leak-barrier flaps with the front waist region and the rear waist region respectively.

PANTS-TYPE DISPOSABLE WEARING ARTICLE

BACKGROUND OF THE INVENTION

This invention relates to a pants-type disposable wearing article to absorb and to retain body exudates.

Japanese Patent Application No. 1995-155344A discloses a pants-type disposable diaper generally composed of a pants member comprising a front waist region, a rear waist region and a crotch region extending between these waist regions, and a liquid-absorbent pad comprising a liquid-pervious topsheet, a liquid-impervious backsheet and a liquid-absorbent core interposed between these sheets so as to be attached to the inner side of the pants wherein the absorbent pad includes a pair of end flaps extending outward from front and rear ends of the core and a pair of side flaps extending outward from transversely opposite side edges of the core and the end flaps are connected to the pants in the front and rear waist regions.

The absorbent pad is provided with a pair of leak-barrier flaps extending outside from the side edges of the core. Free side edge portions of the respective leak-barrier flaps are provided with elastically stretchable members bonded in a stretched state thereto. With this diaper of prior art, the elastic members contract as the absorbent pad is curved its longitudinal direction with the topsheet inward and contraction of the elastic members cause the free side edge portions to rise on the core. In the pad, the free side edge portions of the respective leak-barrier flaps form barriers against body exudates and eliminate the possibility that the body exudates might leak from the crotch region.

In the case of the article disclosed in the above-cited Publication, longitudinally opposite end portions of the leak-barrier flaps attached to the absorbent pad are laid down outwardly in the transverse direction of the pad and bonded to the side flaps in such a laid down state. Consequently, so far as the longitudinally opposite end portions are concerned, the leak-barrier flaps can not function as the barriers against the body exudates and leakage of the body exudates can not be prevented in the front and rear waist regions of the pants. In addition, depending upon a stretch stress of the elastic members attached to the respective leak-barrier flaps, the free side edge portions of the leak-barrier flaps may sometimes be unable to rise on the core.

SUMMARY OF THE INVENTION

It is an object of this invention to provide a pants-type disposable wearing article improved so that a pair of leak-barrier flaps can reliably rise from side edges of a core over the full length thereof as viewed in the longitudinal direction of the flaps to prevent leakage of body exudates not only from a crotch region but also front and rear waist regions.

According to this invention, there is provided a pants-type disposable wearing article having a front waist region, a rear waist region, a crotch region, a waist-hole and a pair of leg-holes and including a holder means and an absorbent pad means wherein the holder means has the front and rear waist regions both of which are cooperating to define the waist-hole and the absorbent pad means comprises a liquid-pervious topsheet, a liquid-impervious backsheet, a liquid-absorbent core interposed between the topsheet and backsheet and having opposite side edges extending in a longitudinal direction of the absorbent pad means and has in the longitudinal direction the crotch region extending to the front and rear waist regions respectively so as to cooperate

DETAILED DESCRIPTION OF THE PREFERRED EMBODIMENTS

Details of the pants-type disposable wearing article according to this invention will be more fully understood from the description given hereunder in reference to the accompanying drawings.

Figure 1:
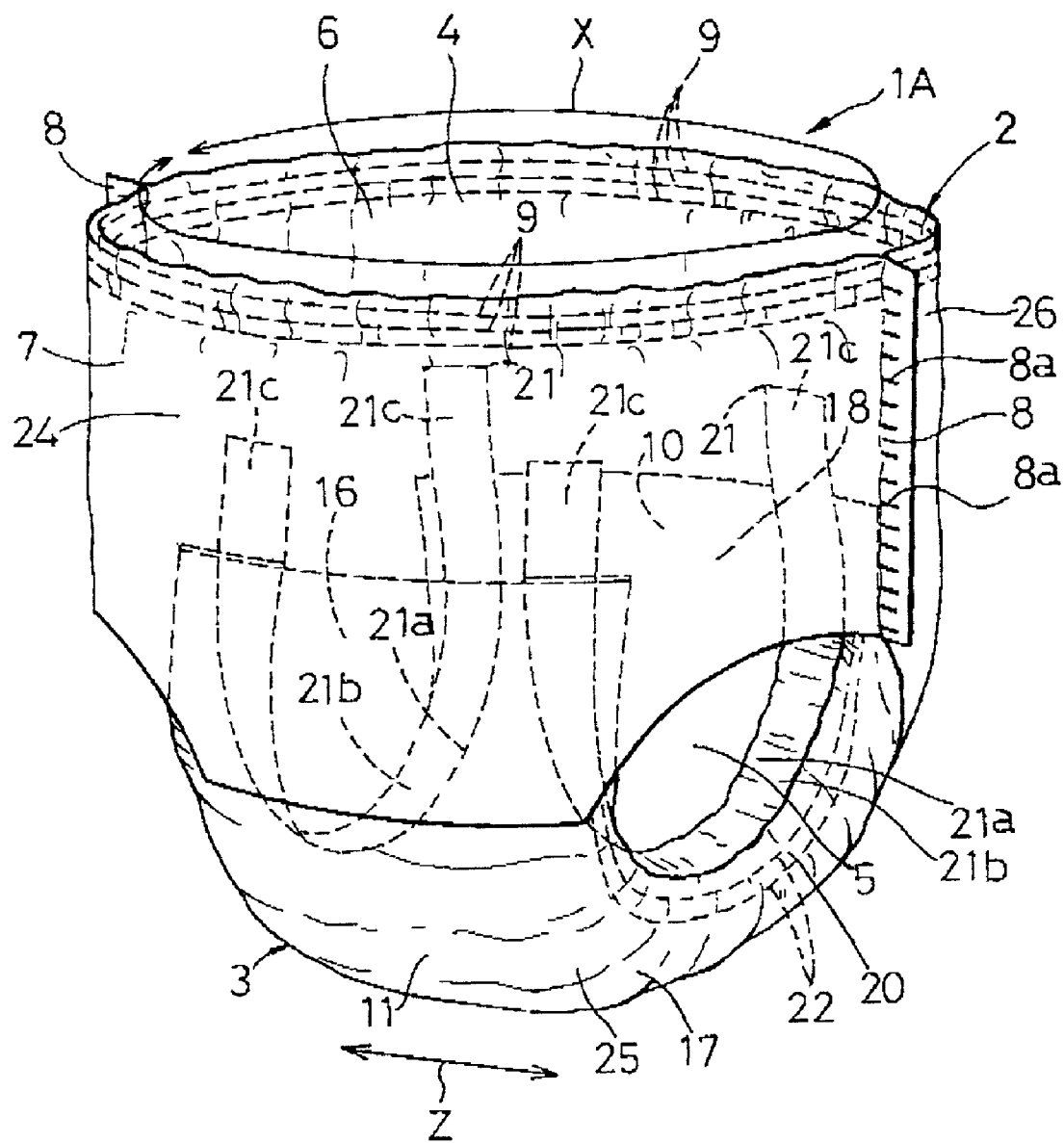
FIG. 1 is a perspective view of the disposable wearing article.
Figure 2:
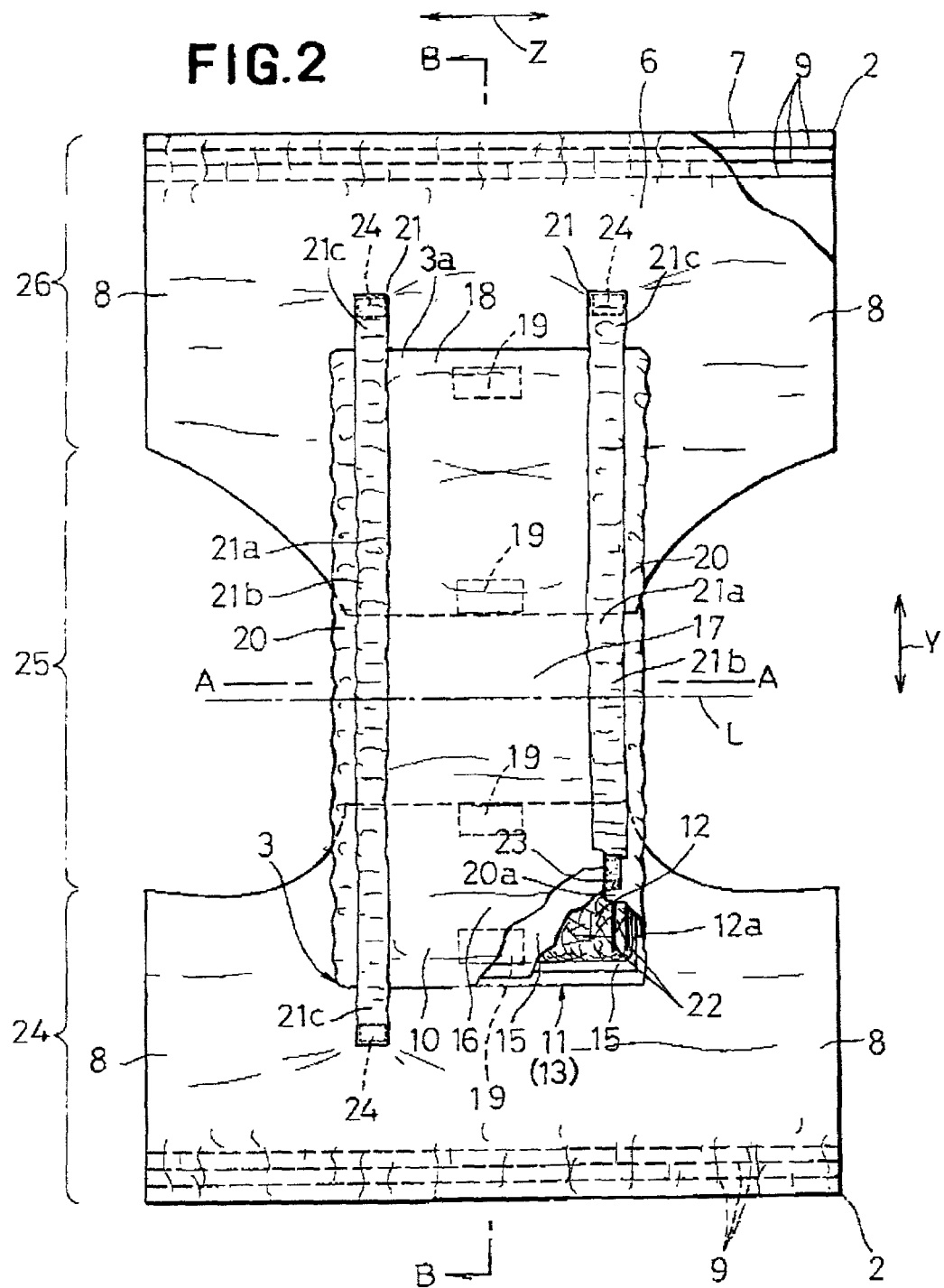
FIG. 2 is a partially cutaway plan view showing the article before the front and rear waist regions of the article are connected to each other.
Figure 3:
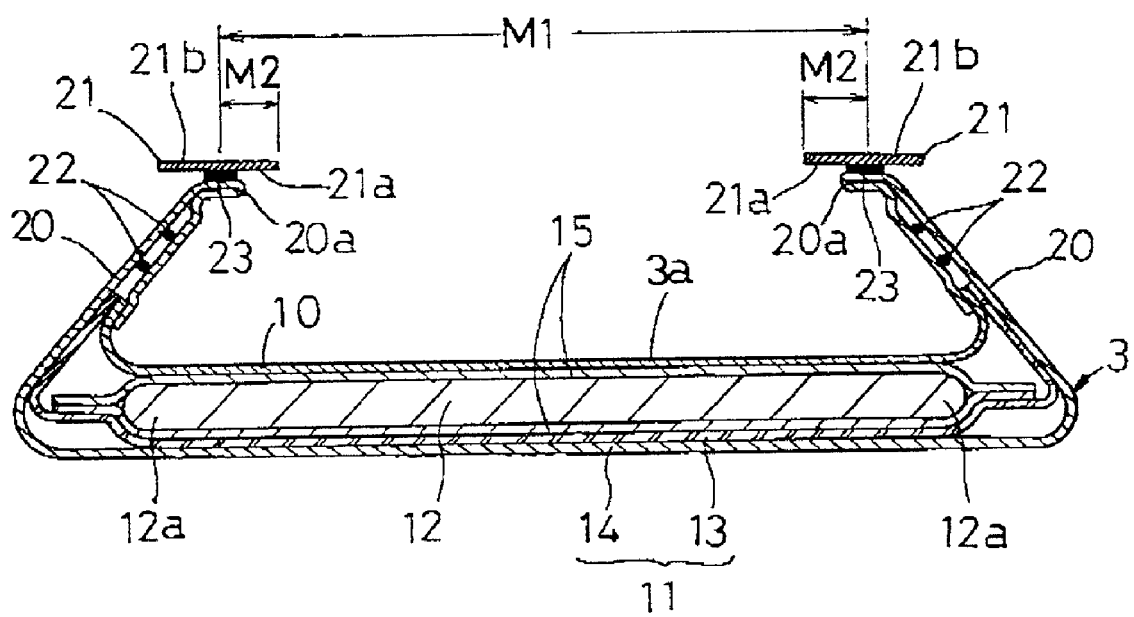
FIG. 3 is a side view showing a cut surface taken along a line A—A in FIG. 2.
Figure 4:
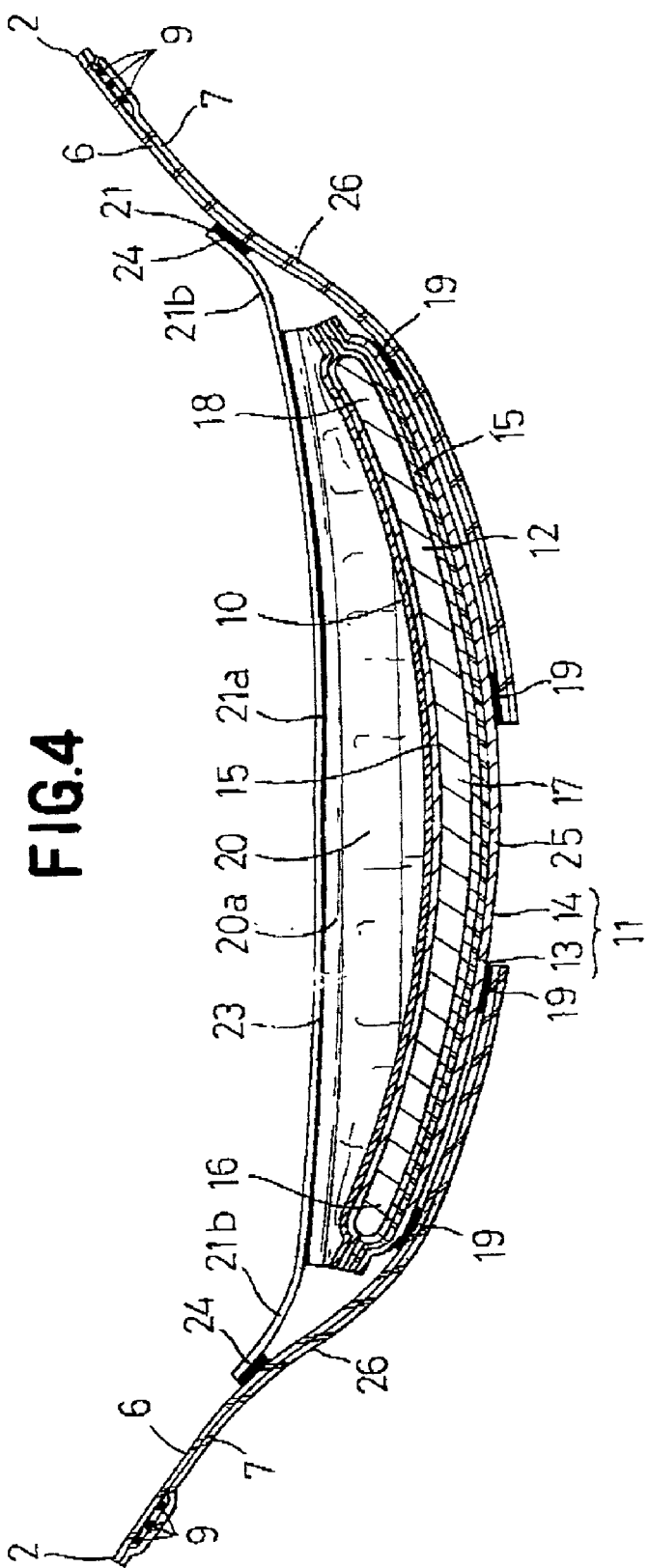
FIG. 4 is a sectional view taken along a line B—B in FIG. 2, showing the article as slightly curved in its longitudinal direction.

FIG. 1 is a perspective view of a disposable wearing article 1A, FIG. 2 is a partially cutaway plan view showing the article 1A before front and rear waist regions 24, 26 are connected to each other, FIG. 3 is a side view showing a cut surface taken along a line A—A in FIG. 2 and FIG. 4 is a sectional view taken along a line B—B in FIG. 2, showing the article 1A as slightly curved in its longitudinal direction. In the article 1A of FIG. 1, a waist-surrounding direction is indicated by an arrow X, a thigh-surrounding direction is indicated by an arrow Y and a transverse direction is indicated by an arrow Z. In the article 1A of FIG. 2, a longitudinal direction is indicated by an arrow Y and the transverse direction by the arrow Z. Expression "inner surfaces" of a skin covering sheet 2 and a liquid-pervious topsheet 10, and a liquid-impervious backsheet 11 as used herein should be understood to be those facing a core 12 and expression "outer surfaces" of these sheets 2, 10, 11 should be understood to be those facing away from the core 12.

The article 1A comprises a skin covering sheet 2 and an absorbent pad 3 held by the skin covering sheet 2 in such a manner that it is connected to the inside surface of the skin covering sheet 2. In another aspect, the article 1A comprises a front waist region 24, a rear waist region 26 and a crotch region 25 extending between these waist regions 24, 26. In the article 1A, the covering sheet 2 is extending around the waist of a wearer of the article 1A and defines a waist-hole 4. The covering sheet 2 works as a holder means to keep the absorbent pad 3 on the wearer of the article 1A and cooperates with the absorbent pad 3 to define a pair of leg-holes 5. The absorbent pad 3 works as an absorbent pad means to absorb body exudates of the wearer. As will be best seen in FIG. 2, the article 1A presents an hourglass-shaped figure as viewed in this plan view.

The skin covering sheet 2 has two elastically stretchable sheets 6, 7 overlaid each other. The skin covering sheet 2 constitutes the front waist region 24, the rear waist region 26 and a part of the crotch region 25 of the article 1A. The front and rear waist regions 24, 26 are put flat and connected together along transversely opposite side edges 8 by means of a plurality of heat-sealing area 8a arranged intermittently in the vertical direction along the respective side edges 8.

A plurality of elastic members 9 associated with the waist-hole 4 extending in a direction along a peripheral edge of the waist-hole 4 are interposed between the sheets 6, 7 and bonded to these sheets 6, 7 in a stretched state.

The absorbent pad 3 comprises the liquid-pervious topsheet 10 facing a wearer's skin, the liquid-impervious backsheet 11 facing away from the wearer's skin and a liquid-absorbent core 12 interposed between these two sheets 10, 11. The backsheet 11 has two component sheets 13, 14 overlaid each other. The core 12 is entirely covered with and bonded to a tissue paper 15 and bonded to respective inner surfaces of the top- and backsheets 10, 11 with the tissue paper 15 therebetween.

The absorbent pad 3 has front and rear ends 16, 18 locating in the longitudinal direction of the pad 3 and lying inside of the front and rear waist regions 24, 26, respectively, and the pad 3 has an intermediate zone 17 extending between these front and rear ends 16, 18. Of the absorbent pad 3, the front and rear ends 16, 18 are bonded to the inner surfaces of the front and rear waist regions 24, 26 of the skin covering sheet 2 and the intermediate zone 17 is bonded to the inner surfaces of the crotch regions 25 of the front waist region 24 and the rear waist region 26 of the skin covering sheet 2.

The absorbent pad 3 has a pair of leak-barrier flaps 20 lying immediately outside of transversely opposite side edges 12a of the core 12 and extending in the longitudinal direction of the absorbent pad 3 and a pair of ribbon-like suspenders 21 attached to the top edges 20a of the respective leak-barrier flaps 20 and extending in the longitudinal direction of the absorbent pad 3.

The leak-barrier flaps 20 rise upward from the side edges 12a of the core 12. More specifically, these leak-barrier flaps 20 of FIG. 3 are arranged obliquely inward as viewed in the transverse section of the absorbent pad 2. The respective leak-barrier flaps 20 are provided with a plurality of elastically stretchable members 22 extending in the longitudinal direction of the absorbent pad 3 and bonded in a stretched state to the flaps 20.

As will be seen in FIG. 3, the leak-barrier flaps 20 are respectively formed by transversely opposite lateral portions of the backsheet 11 extending outwardly beyond the side edges 12a of the core 12 in the transverse direction. In the leak-barrier flaps 20, the one component sheet 14 of the backsheet 11 is folded back at the respective top edges 20a of the leak-barrier flaps 20. Transversely opposite lateral portions of the topsheet 10 extending outwardly beyond the side edges 12a of the core 12 are partially interposed between the component sheets 13, 14 of the backsheet 11 and bonded to these component sheets 13, 14.

The ribbon-like suspenders 21 are made of an elastically stretchable sheet in the longitudinal direction of the absorbent pad 3 and bonded to the respective top edges 20a of the leak-barrier flaps 20 by means of hot melt adhesive 23. Each of the suspenders 21 has overhanging extensions 21a, 21b extending inwardly and outwardly, respectively, from the associated top edge 20a of the leak-barrier flaps 20, and extensions 21c extending outwardly from the front and rear ends 16, 17 of the absorbent pad 3. These suspenders 21 are attached in a stretched or non-stretched state to the inner surface of the skin covering sheet 2 in such a manner that the extensions 21c of the respective suspenders 21 are bonded to the skin covering sheet 2 in the front and rear waist regions 24, 26 thereof by means of hot melt adhesive 24.

To complete the article 1A from its state as shown in FIG. 2 to its state as shown in FIG. 1, the article 1A of FIG. 2 is folded along a transverse center line L bisecting the longitudinal dimension of the article 1A of FIG. 2 with the topsheet 10 inside and then the front and rear waist regions 24, 26 are bonded together along the transversely opposite side edge portions 8 of these waist regions 24, 26.

In the article 1A of FIG. 1, the suspenders 21 function as means to suspend the leak-barrier flaps 20 above the side edges 12a of the core 12 and, in other words, ensure the leak-barrier flaps 20 to rise from the side edges 12a of the core 12. In the case of this article 1A, the whole lengths of the top edges 20a of the leak-barrier flaps 20 are not bonded to the inside surface 3a of the absorbent pad 3 so that the leak-barrier flaps 20 can rise over the full length thereof in the longitudinal direction of the absorbent pad 3. The leak-barrier flaps 20 form barriers against body exudates and prevent the leakage of the exudates from the front and rear waist regions 24, 26 as well as from the crotch region 25 of the article 1A. Owing to the suspenders 21, the leak-barrier flaps 20 are generally tilted inwardly in the transverse direction of the absorbent pad 3 and cannot be easily laid down outwardly in the transverse direction of the absorbent pad 3.

In the article 1A, the extensions 21a of the respective suspenders 21 extending inwardly to the transverse direction of the absorbent pad 3 from the top edges 20a of the respective leak-barrier flaps 20 form second barriers extending substantially in parallel to the upper surface of the core 12 which faces the topsheet 10. These second barriers prevent body exudates from flowing over the leak-barrier flaps 20 even if the leak-barrier flaps 20 are of a relatively small height dimension.

Figure 5:
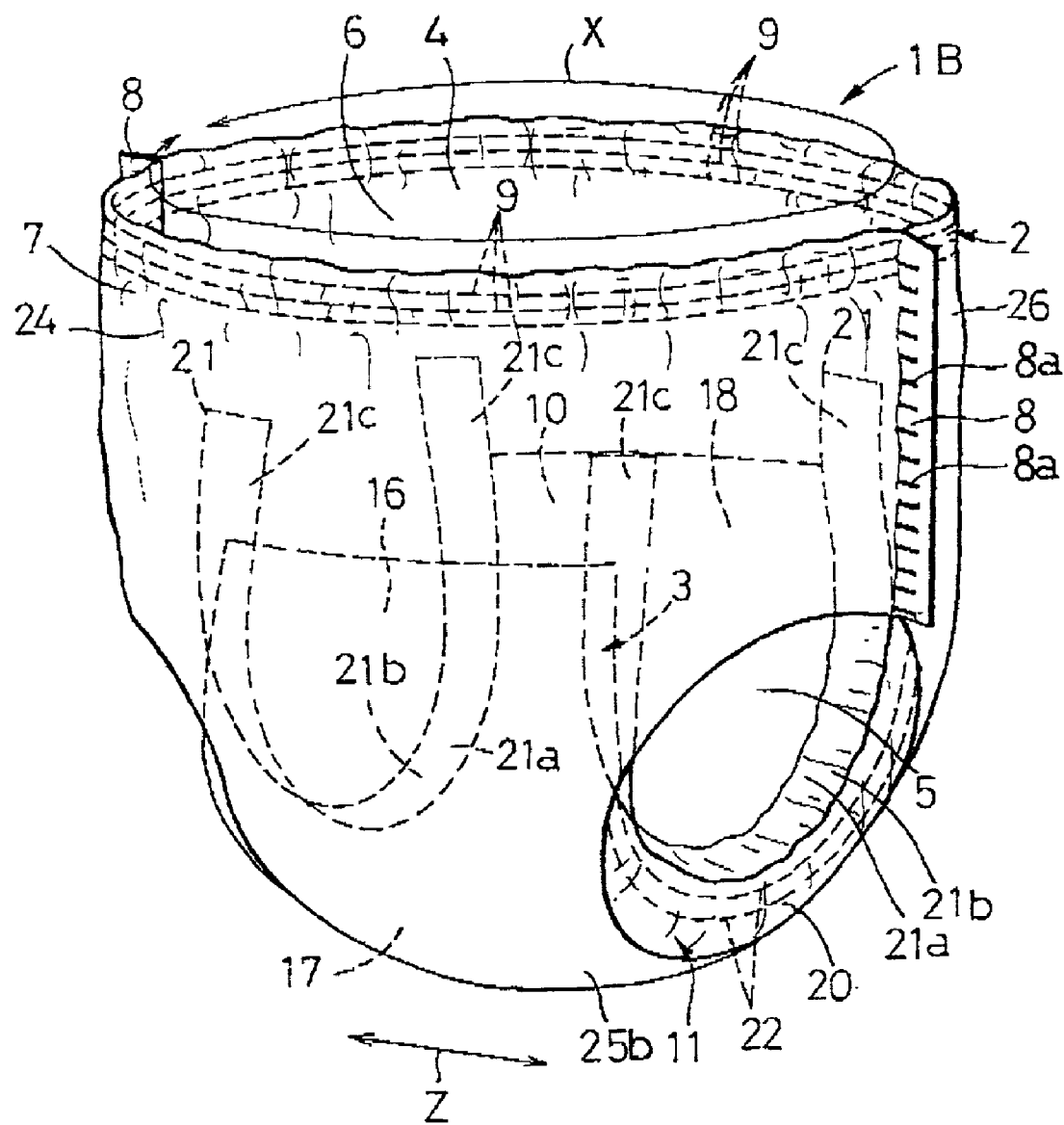
FIG. 5 is a perspective view of another embodiment of the disposable wearing article.
Figure 6:
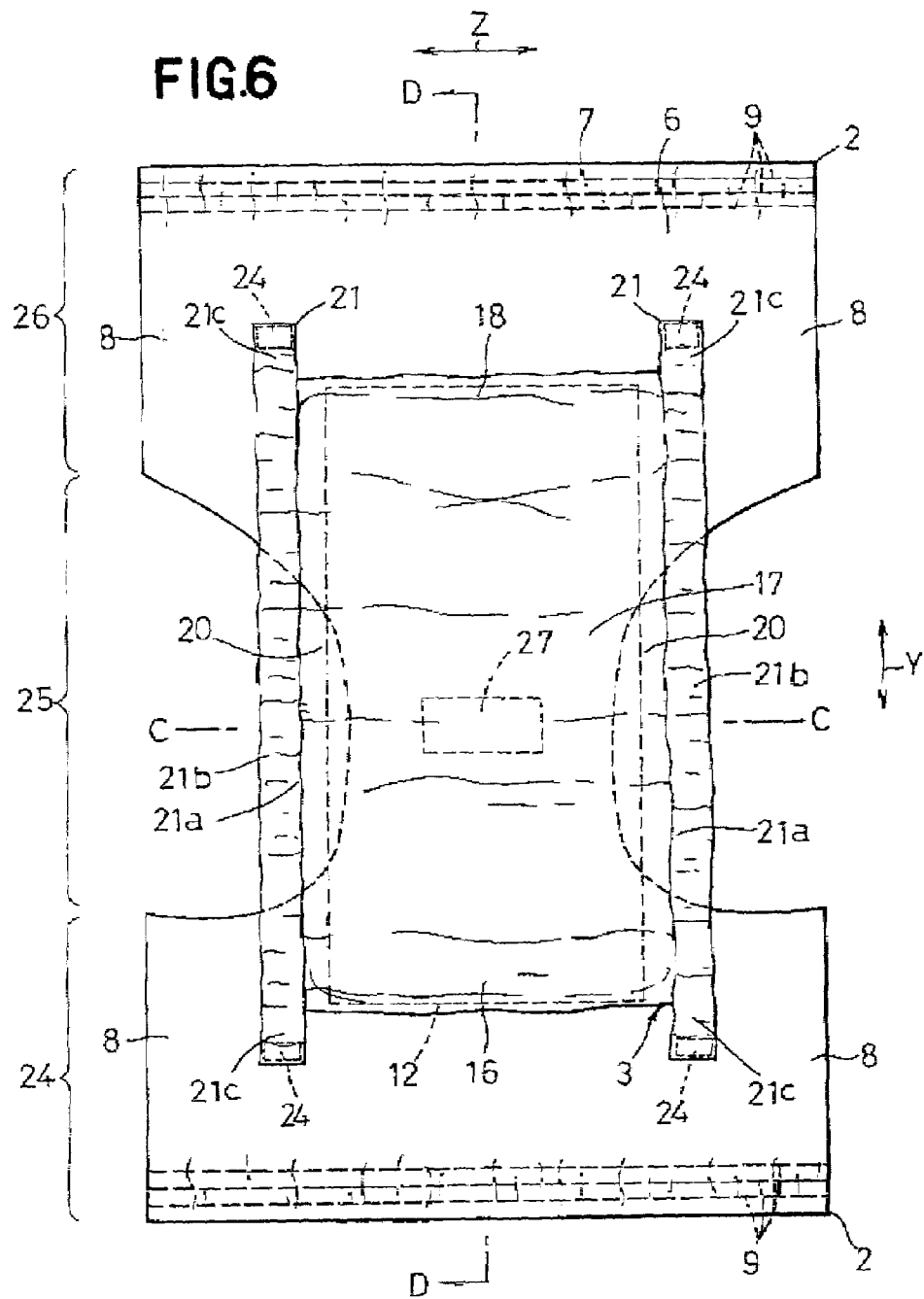
FIG. 6 is a partially cutaway plan view showing this embodiment of the article before the front and rear waist regions of the article are connected to each other.
Figure 7:
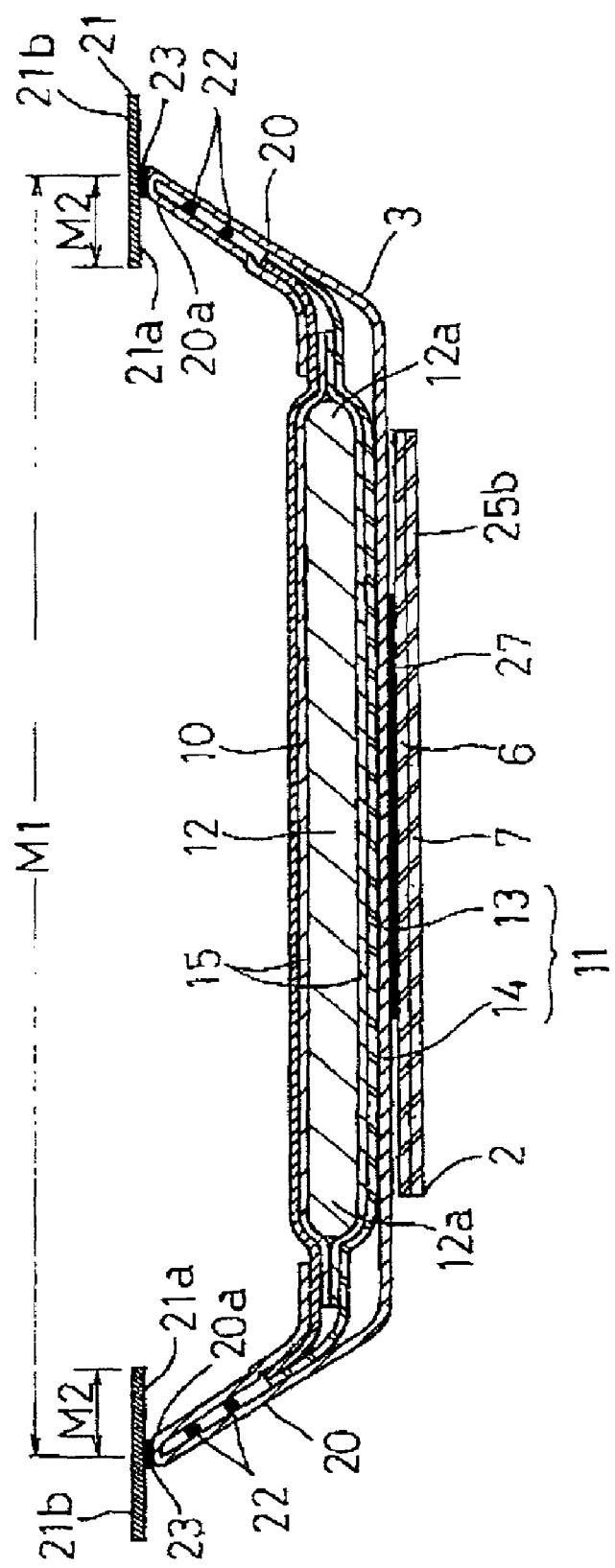
FIG. 7 is a side view showing a cut surface taken along a line C—C in FIG. 6.
Figure 8:
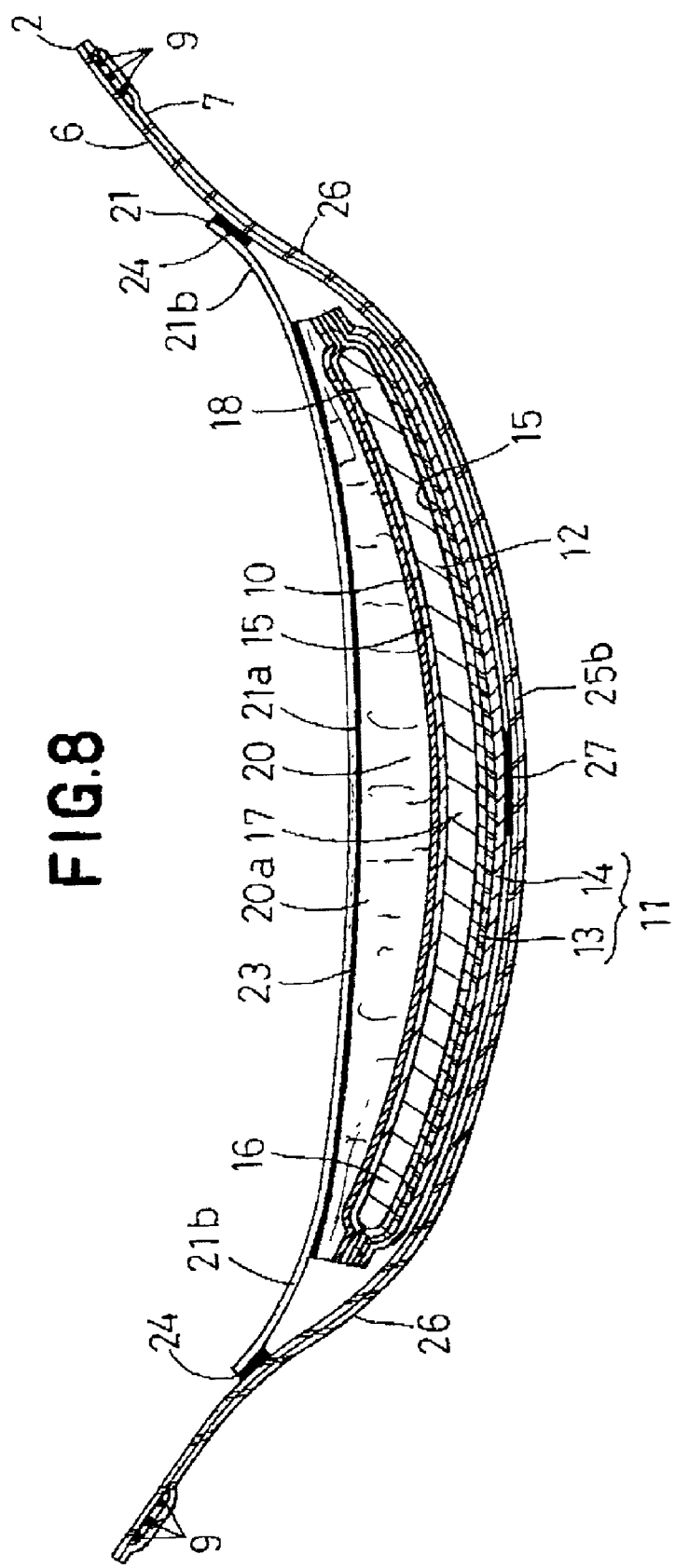
FIG. 8 is a sectional view taken along a line D—D in FIG. 6, showing the article as slightly curved in its longitudinal direction.

FIG. 5 is a perspective view of another embodiment 1B of the disposable wearing article, FIG. 6 is a partially cutaway plan view showing this embodiment of the article 1B before the front and rear waist regions 24, 26 are connected to each other, FIG. 7 is a side view showing a cut surface taken along a line C—C in FIG. 6 and FIG. 8 is a cross-sectional view taken along a line D—D in FIG. 6, showing the article 1B as slightly curved in its longitudinal direction. In the article 1B of FIG. 5, the waist-surrounding direction is indicated by an arrow X, and the transverse direction is indicated by an arrow Z. In FIG. 6, the longitudinal direction is indicated by an arrow Y.

The article 1B is similar to the article 1A shown in FIG. 1 in that the article 1B comprises the skin covering sheet 2 and the absorbent pad 3 connected to the skin covering sheet 2. The article 1B shown in FIG. 5 is distinguished from the article 1A shown in FIG. 1 in its arrangement as will be described below.

The skin covering sheet 2 of the article 1B forms the front and rear waist regions 24, 26 and a crotch region 25b extending between these waist regions 24, 26 and lying on the outer surface of the crotch region 25 of the absorbent pad 3. The front waist region 24 and the rear waist region 26 are bonded together along the transversely opposite side edge portions 8 by means of a plurality of heat-sealing areas 8a arranged intermittently in the vertical direction along these side edge portions 8. In other words, the skin covering sheet 2 itself presents a pants-type shape. As will be best seen in FIG. 6, the skin covering sheet 2 delineates, in its crotch region 25, substantially circular arcs which are convex in the transverse direction of the article 1B.

The intermediate zone 17 of the absorbent pad 3 is attached to the inside surface of the crotch region 25a of the skin covering sheet 2 by means of hot melt adhesive 27. In the absorbent pad 3, the leak-barrier flaps 20 rise from the side edges 12a of the core 12. The leak-barrier flaps 20 are generally tilted outwardly with respect to the side edges 12a of the core 12.

The extensions 21c of the suspenders 21 are bonded to the skin covering sheet 2 in its front and rear waist regions 24, 26 at positions biased from the longitudinal center line (not shown) of the skin covering sheet 2 to the transversely opposite side edge portions 8. The suspenders 21 are connecting substantially in a stretched or non-stretched state the top edges 20a of the leak-barrier flaps 20 with the inner surface of the skin covering sheet 2.

The article 1B is similar to the article 1A shown in FIG. 1 in that the suspenders 21 function as means to suspend the leak-barrier flaps 20 in such a manner that the leak-barrier flaps 20 rise from the side edges 12a of the core 12. Also in the case of this article 1B, the leak-barrier flaps 20 form barriers to prevent the leakage of the body exudates from the front and rear waist regions 24, 26 as well as from the crotch region 25 of the article 1B.

In the article 1B, the leak-barrier flaps 20 are generally tilted outwardly with respective to the side edges 12a of the core 12 so that an area of the topsheet 10 facing the upper surface of the core 12 is fully exposed between the leak-barrier flaps 20. In the article 1B, a width M1 between the opposite top edges 20a of the leak-barrier flaps 20 is larger than that in the article 1A shown in FIG. 1 and therefore the body exudates can be reliably received between the leak-barrier flaps 20. In this way, excretion of the body exudates might not leak out onto the areas outside the leak-barrier flaps 20.

In the article 1B, even if the leak-barrier flaps 20 are laid down outwardly in the transverse direction of the absorbent pad 3, the body exudates might not leak from the front and rear waist regions 24, 26 as well as from the crotch region 25 because the overhanging extensions 21a of the respective suspenders 21 extending inwardly from the top edges 20a of the respective leak-barrier flaps 20 in the transverse direction of the absorbent pad 3 form the second barriers.

With both the article 1A and the article 1B, the suspenders 21 are stretched in the longitudinal direction and the ribbon-like suspenders 21 having the overhanging extensions 21a, 21b thereof come in close contact with the wearer's thighs as these articles are worn. Consequently, no gaps are formed between the wearer's thighs and the suspenders 21 and the leakage of the body exudates from the crotch region 25 is reliably prevented.

In these articles 1A, 1B, each of the overhanging extensions 21a of the suspenders 21 extending inwardly from the top edges 20a of the associated leak-barrier flaps 20 in the transverse direction preferably has a width M2 in a range from 1 to 4 cm. The overhanging extension 21a with its width M2 less than 1 cm would not sufficiently function as the second barrier. In such a case, the body exudates may flow over the leak-barrier flaps 20 or the body exudates may leak from the front and rear waist regions 24, 26 as well as from the crotch region 25 when the leak-barrier flaps 20 are laid down outwardly to the transverse direction of the absorbent pad 3. The overhanging extension 21a with its width M2 exceeding 4 cm would cover the upper surface of the core 12 and unacceptably reduce the width dimension M1 between the opposite top edges 20a of the leak-barrier flaps 20. As a result, it may be impossible to retain the body exudates between the leak-barrier flaps 20.

In these articles 1A, 1B, it is possible to form the skin covering sheet 2 and the suspenders 21 using non-stretchable sheets. When the suspenders 21 comprise the non-stretchable sheets, the suspenders 21 are provided with elastically stretchable members extending in the longitudinal direction bonded in a stretched state to the suspenders 21. While the leak-barrier flaps 20 of these articles 1A, 1B have been illustrated-and described as they are formed by the lateral portions of the backsheet 11, it is also possible to form these leak-barrier flaps 20 using substantially liquid-impervious and stretchable or non-stretchable sheets attached to the lateral portions of the top- and backsheets 10, 11.

The topsheet 10 may be formed of a hydrophilic fibrous nonwoven fabric or a finely porous plastic film. The backsheet 11 may be formed of either of a hydrophobic fibrous nonwoven fabric, a breathable but liquid-impervious plastic film, two-layers of a nonwoven fabric laminated with a hydrophobic fibrous nonwoven fabric, and a composite sheet consisting of a hydrophobic fibrous nonwoven fabric and a breathable but liquid-impervious plastic film bonded to this hydrophobic fibrous nonwoven fabric.

It is also possible to form the backsheet 11 using a composite nonwoven fabric with a highly water-resistant fibrous nonwoven fabric made by melt-blown process sandwiched by two layers of spun bonded fibrous nonwoven fabric having high strength and flexibility.

Nonwoven fabric used herein may be selected from a group of nonwoven fabrics manufactured by such a process as spun lacing-, needle punching-, melt blowing-, thermal bonding-, spun bonding-, chemical bonding- and air through-processes. Component fiber of such a nonwoven fabric may be selected from a group of materials including polyolefine-, polyester- and polyamide-based fibers and core-sheath type or side-by-side type conjugated fibers of polyethylene/polypropylene or polyethylene/polyester.

The skin covering sheet 2 as well as the suspenders 21 may be formed with any one of the materials including stretchable hydrophobic fibrous nonwoven fabric, stretchable and breathable but liquid-impervious plastic film, two layers of stretchable hydrophobic fibrous nonwoven fabric laminated with each other, and composite sheet consisting stretchable hydrophobic fibrous nonwoven fabric and stretchable, breathable but liquid-impervious plastic film laminated with each other.

The stretchable fibrous nonwoven fabric may be any one of melt-blown nonwoven fabric and spun bonded nonwoven fabric. As the component fiber of the stretchable nonwoven fabric, stretchable fiber obtained by melt-spinning a thermoplastic elastomer resin can be used. Alternatively, a composite nonwoven fabric consisting of first hydrophobic fibrous nonwoven fabric of thermoplastic elastomer resin fiber and second hydrophobic fibrous nonwoven fabric of a crimped fiber obtained by melt-spinning a thermoplastic synthetic resin selected from a group of polypropylene, polyethylene and polyester wherein the second hydrophobic fibrous nonwoven fabric is bonded to at least one surface of the first hydrophobic fibrous nonwoven fabric.

When the skin covering sheet 2 and the suspenders 21 are formed of non-stretchable sheets, the non-stretchable sheets may of the same material as that of the backsheet 12.

The core 12 comprises a mixture of fluff pulp and super-absorbent polymer particles or a mixture of fluff pulp, super-absorbent polymer particles and thermoplastic synthetic resin fiber, in both cases, compressed to a desired thickness. As the polymer particles, starch-, cellulose- or synthetic polymer-based particles may be used.

Bonding of the absorbent pad 3 to the skin covering sheet 2 and bonding of the suspenders 21 to the leak-barrier flaps 20 may be carried out using hot melt adhesive, heat-welding or ultrasonic welding. These adhesive and welding are applicable to bonding of the top- and backsheets 10, 11, attaching of the elastic members 9, 22 and bonding of the core 12.

The pants-type disposable wearing article according to this invention ensures the leak-barrier flaps to rise from the side edges of the core since the leak-barrier flaps are attached to the suspenders. This wearing article enables also the leak-barrier flaps to rise over the full length thereof in the longitudinal direction since the top edges of the leak-barrier flaps are not bonded to the inside surface of the absorbent pad. With this novel article, the barriers formed by the leak-barrier flaps effectively function to prevent the leakage of the body exudates from the front and rear waist regions as well as from the crotch region. Furthermore, the overhanging extensions of the suspenders extending inwardly from the top edges of the leak-barrier flaps in the transverse direction of the absorbent pad form the second barriers extending substantially in parallel to the core. These second barriers reliably prevent the body exudates from flowing over the leak-barrier flaps and, even if the leak-barrier flaps are laid down outwardly with respect to the absorbent pad in the transverse direction, the body exudates does not leak from the front and rear waist region as well as from the crotch region.

According to this invention with the leak-barrier flaps tilted outwardly with respect to the side edges of the core, the width between the opposite top edges of the leak-barrier flaps is sufficiently enlarged to retain the body exudates between the leak-barrier flaps. Therefore, the body exudates does not leak from the inside of the leak-barrier flaps.

What is claimed is:

1. A pants-type disposable wearing article comprising:
   a float waist region;
   a rear waist region;
   a crotch region;
   a waist-hole;
   a pair of leg-holes;
   an absorbent pad assembly; and
   a holder assembly for holding the absorbent pad assembly,
   wherein the holder assembly has front and rear waist regions which define the waist hole when the front and rear waist regions of the holder assembly are coupled together,
   the absorbent pad assembly comprises:
      a liquid-pervious topsheet;
      a liquid-impervious backsheet;
      a liquid-absorbent core interposed between the topsheet and backsheet and having opposite side edges extending in a longitudinal direction;
      a crotch region extending between the front and rear waist regions of the holder assembly so as to define the pair of leg-holes together with the holder assembly; and
   front and rear ends that are attached to the front and tear waist regions respectively, the pants-type disposable wearing article further comprising:
      a pair of leak-barrier flaps included on the absorbent pad assembly and located immediately outside of the opposite side edges of the liquid absorbent core, the pair of leak-barrier flaps extending in the longitudinal direction of the absorbent pad assembly and being configured to rise from the opposite side edges; and
      suspenders lying on top edges of leak-barrier flaps, extending outwardly of the leak-barrier flaps in the longitudinal direction of the absorbent pad assembly, and connecting the leak-barrier flaps with the front waist region and the rear waist regions, the suspenders including skin contacting surfaces which are configured to contact the skin of a wearer of the pants-type disposable wearing article.

2. The article according to claim 1, wherein the suspenders comprise ribbon-like shapes.

3. The article according to claim 2, wherein the suspenders include overhanging portions that extend at least inwardly from top edges of the leak barrier flaps in the transverse direction of the absorbent pad assembly.

4. The article according to claim 3, wherein the suspenders include overhanging portions that extend outwardly from the top edges of the leak-barrier flaps in the transverse direction of the absorbent pad assembly.

5. The article according to claim 1, wherein the suspenders are elastically stretchable in the longitudinal direction of the absorbent pad assembly.

6. The article according to claim 1, wherein the suspenders extend along entire lengths of the top edges of the leak barrier flaps.

7. The article according to claim 1, wherein the leak barrier flaps and the suspenders are made of elastically stretchable sheets.

8. The article according to claim 1, wherein the holder assembly has a crotch region lying on the crotch region of the absorbent pad assembly so as to form a pants-type shape.

* * * * *

UNITED STATES PATENT AND TRADEMARK OFFICE
CERTIFICATE OF CORRECTION

PATENT NO. : 7,014,632 B2  Page 1 of 1
APPLICATION NO. : 10/146226
DATED : March 21, 2006
INVENTOR(S) : Shunsuke Takino and Toshifumi Otsubo It is certified that error appears in the above-identified patent and that said Letters Patent is hereby corrected as shown below:

Column 7,

Line 50, should be changed from
       "a float waist region;"
to
       --a front waist region;--

Signed and Sealed this

Fourth Day of July, 2006

JON W. DUDAS
*Director of the United States Patent and Trademark Office*